US008138366B2

United States Patent
Arava et al.

(10) Patent No.: US 8,138,366 B2
(45) Date of Patent: Mar. 20, 2012

(54) PROCESS FOR THE PREPARATION OF MALATHION AND ITS INTERMEDIATE

(75) Inventors: Veera Reddy Arava, Andhra Pradesh (IN); Vaishali Nadkarni, Andhra Pradesh (IN); Venkateswarlu Jasti, Andhra Pradesh (IN)

(73) Assignee: Suven Life Sciences Limited, Hyderabad (IN)

( * ) Notice: Subject to any disclaimer, the term of this patent is extended or adjusted under 35 U.S.C. 154(b) by 268 days.

(21) Appl. No.: 12/668,149

(22) PCT Filed: Apr. 28, 2008

(86) PCT No.: PCT/IN2008/000270
§ 371 (c)(1),
(2), (4) Date: Jan. 7, 2010

(87) PCT Pub. No.: WO2009/007998
PCT Pub. Date: Jan. 15, 2009

(65) Prior Publication Data
US 2010/0204501 A1    Aug. 12, 2010

(30) Foreign Application Priority Data
Jul. 9, 2007  (IN) ............................ 1471/CHE/2007

(51) Int. Cl.
*C07F 9/165*   (2006.01)
(52) U.S. Cl. ...................................... 558/112
(58) Field of Classification Search .................. 558/112
See application file for complete search history.

(56) References Cited

U.S. PATENT DOCUMENTS

| | | | |
|---|---|---|---|
| 2,578,652 A | | 12/1951 | Cassaday |
| 2,879,284 A | | 3/1959 | Divine |
| 3,403,201 A | | 9/1968 | Adrian |
| 3,463,841 A | | 8/1969 | Backlund |
| 3,470,272 A | | 9/1969 | Melton |
| 3,671,612 A | * | 6/1972 | Roszinski et al. ............ 558/133 |
| 4,367,180 A | | 1/1983 | Rouy |
| 4,681,964 A | | 7/1987 | Annarelli |
| 2007/0010496 A1 | | 1/2007 | Gutman |

OTHER PUBLICATIONS

Gonzalez-Velasco et al. Ind. Eng. Chem. Res. 1996, 35, 4389-4393.*
Keadtisuke et al., "Liver Damage Induced in Rats by Malathion Impurities", Toxicology Letters, 52: 35-46 (1990).
Rodgers et al., "Protection From O,O,S-trimethyl phosphorothioate-induced immune suppression", Immunopharmacology, 17:131-140 (1989).
Polec et al., "Enantiomers of O,O-Dialkyl Malathion Analogs. Synthesis and Toxicological Characteristics", Organika—Prace Nauk. Inst. Przem. Org: 1997-1998, Cz.11, No. 2: 7-20 (1998) PL ISSN 0137-9933.
Lefferts et al., "Oxy and thio phosphorous acid derivatives of tin.1. Trioorganotin(IV)dithiophosphate esters", Inorg. Chem. 19(6):1662-1670 (1980) XP002496618.
Berkman et al., "Synthesis of Chiral Malathion and Isomalathion", Tetrahedron Letters, 33(11): 1415-18 (1992).
Emmer et al., Zum Verhalten Von Mono- Und Diolefinen Gegenuber Thallium(III)Trifluoracetat, Tetrahedron, 33(11): 1415-18 (1977).
International Search Report issued in counterpart PCT Appln No. PCT/IN2008/000270, 2008.
Written Opinion issued in counterpart PCT Appln No. PCT/IN2008/000270, 2008.
International Preliminary Report on Patentability issued in counterpart PCT Appln No. PCT/IN2008/000270, 2009.

* cited by examiner

*Primary Examiner* — Joseph Kosack
*Assistant Examiner* — Matthew Coughlin
(74) *Attorney, Agent, or Firm* — IpHorgan Ltd.

(57) ABSTRACT

The present invention relates to the improved process for the preparation of highly pure form of S-[1,2-(dicarbethoxy)-ethyl]O,O-dimethyl phosphorodithioate having formula (I). The compound of formula (I) has adopted name "Malathion". The present invention also relates to the novel process of preparing intermediate O,O-dimethyldithiophosphoric acid of formula (II), which is useful in the preparation of Malathion.

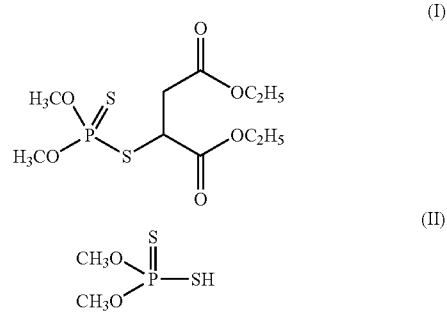

15 Claims, No Drawings

PROCESS FOR THE PREPARATION OF MALATHION AND ITS INTERMEDIATE

CROSS-REFERENCE TO RELATED APPLICATIONS

This is a Section 371 National Stage application based on PCT International Application No. PCT/IN2008/000270, filed on Apr. 28, 2008, claiming priority from Indian Patent Application No. 1471/CHE/2007 filed on Jul. 9, 2007, the contents of both applications hereby being incorporated by reference.

FIELD OF INVENTION

The present invention relates to the improved process for the preparation of highly pure form of S-[1,2-(dicarbethoxy)-ethyl]O,O-dimethyl phosphorodithioate having formula (I).

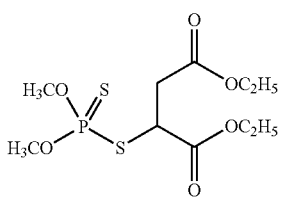
(I)

The compound of formula (I) has adopted name "Malathion". The present invention also relates to the novel process of preparing intermediate O,O-dimethyldithiophosphoric acid of formula (II), which is useful in the preparation of Malathion.

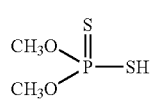
(II)

The Malathion prepared by the process of this invention is highly storage stable and toxic impurities are much lower than any other commercial preparation available for the pharmaceutical purpose.

BACKGROUND OF THE INVENTION

Various processes for the preparation and/or purification of Malathion are disclosed in the literature. Malathion {CAS Number: 121-75-5} is an organophosphate insecticide that inhibits cholinesterase activity in vivo. The U.S. Food and Drug Administration (FDA) supports the pharmaceutical use of malathion for the treatment for head lice in children. Due to its low toxicity to humans. Malathion may be prepared by reacting O,O-dimethyldithiophosphoric acid (OODMDTPA) with diethyl maleate (U.S. Pat. Nos. 2,578,652, 2,879,284, 3,403,201, 3,463,841, 3,470,272, 4,367180, 2007/0010496 and 4,681,964).

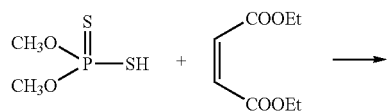

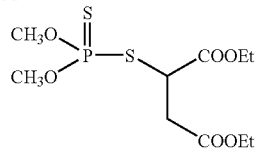

But, still numerous impurities are found in Malathion preparation. Some of these impurities are formed during storage and some are generated during the manufacturing process. Many of these Malathion impurities have been found to be toxic. O,O,S-trimethyl phosphorodithioate (MeOOSPS) and O,S,S-trimethyl phosphorothioate (MeOSSPO) can cause liver damage (Keadtisuke et al, Toxicology letters 52:35-46 (1990) or immune suppression (Rodgers et al, immunopharmacology 17: 131-140 (1989). The toxicity of Iso Malathion is due to its ability to inhibit acetylcholinesterase, in fact Iso Malathion is ~1,000 times as active against acetylcholinesterase as compared with Malathion (Tetrahedron letters 33(11). 1415-18 (1992). Malathion physical properties make it difficult to remove impurities by conventional means for example, because Malathion is liquid at ambient temperature (melting point: 2.9° C.), and crystallization is difficult.

Therefore, we have developed an improved process for the preparation of Malathion for pharmaceutical use. Malathion produced by this method has significantly lower levels of toxic impurities and storage stable, when compared to the any other commercial method available in literature for the pharmaceutical use.

SUMMARY OF THE INVENTION

The present invention relates to the improved process of preparation of Malathion of formula (I),

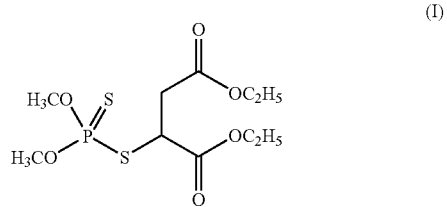
(I)

which comprises:
i) adding methanol to phosphorous sulfide in organic solvent at 25-50° C. for the period of 1.5-2 hours;
ii) stirring the above suspension for the period of 5-6 hours at 50-55° C.;
iii) expelling the H$_2$S gas with nitrogen, after cooling the above suspension to 25-28° C.;
iv) filtering the above suspension to remove insoluble impurities to obtain crude O,O-DMDTPA;
v) the crude O,O-DMDTPA is subjected to dissolution in suitable solvent and ammonia gas is purged to precipitate the pure O,O-DMDTPA.NH$_3$ salt;
vi) the above obtain O,O-DMDTPA.NH$_3$ salt is subjected to neutralization with concentrated sulphuric acid to get O,O-DMDTPA;
vii) the O,O-DMDTPA obtained in the above step is once again purified through ammonia salt formation and neutralization method as mentioned in above steps v) and vi) to get chromatographically pure O,O-DMDTPA;

viii) adding the above obtain pure O,O-DMDTPA to diethyl maleate at low temperature of −30 to −25° C. in four lots, each at regular interval of 20 minutes;

ix) maintain the above reaction mass at temperature of −30 to −25° C. for the period of 4 hours;

x) water wash the above mass to remove O,O-DMDTPA;

xi) treating the above obtain crude Malathion with sulfur reagent at 5 to 10° C. for the period of 13 hours;

xii) crystallizing the above obtained Malathion from methanol at low temperature and xiii) drying the above obtain mass with anhydrous sodium sulphate in isopropanol to obtain Malathion of formula (I).

The present invention also relates to novel process for the preparation of intermediate O,O-DMDTPA having formula (II), which is used in step (viii) of process of preparation of Malathion of formula (I),

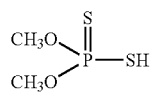
(II)

which comprises:

i) adding methanol to phosphorous sulfide in organic solvent at 25-50° C. for the period of 1.5-2 hours;

ii) stirring the above suspension for the period of 5-6 hours at 50-55° C.;

iii) expelling the $H_2S$ gas with nitrogen, after cooling the above suspension to 25-28° C.;

iv) filtering the above suspension to remove insoluble impurities to obtain crude O,O-DMDTPA;

v) the crude O,O-DMDTPA is subjected to dissolution in ethyl acetate and ammonia gas is purged to precipitate the pure O,O-DMDTPA.$NH_3$ salt;

vi) the above obtain O,O-DMDTPA.$NH_3$ salt is subjected to neutralization with concentrated sulphuric acid to get O,O-DMDTPA and vii) the O,O-DMDTPA obtained in the above step is once again purified through ammonia salt formation and neutralization method as mentioned in above steps v) and vi) to get chromatographically pure product.

In one aspect, the Malathion prepared by the process of present invention having a reduced level of toxic impurities.

In another aspect, the Malathion prepared by the process of present invention is storage stable.

In yet another aspect, the Malathion prepared by this process may be used for pharmaceutical purpose.

In still another aspect, the Malathion prepared by the process of the present invention comprises:

i) greater than 99.5% w/w Malathion and less than 0.09% of Isomalathion, less than 0.03 of O,O,S-trimethyl phosphorodithioate, less than 0.002% of diethyl fumarate, less than 0.1% of unknown impurities and less than 0.21 of total impurities.

ii) water content is less than 0.02%.

DETAILED DESCRIPTION OF THE INVENTION

Accordingly, the present invention relates to the improved process for the preparation of Malathion of formula (I),

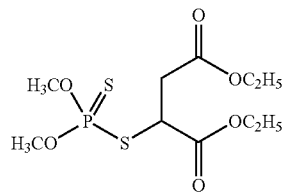
(I)

which comprises:

i) adding methanol to phosphorous sulfide in organic solvent at 25-50° C. for the period of 1.5-2 hours;

ii) stirring the above suspension for the period of 5-6 hours at 50-55° C.;

iii) expelling the $H_2S$ gas with nitrogen, after cooling the above suspension to 25-28° C.;

iv) filtering the above suspension to remove insoluble impurities to obtain crude O,O-DMDTPA;

v) the crude O,O-DMDTPA is subjected to dissolution in suitable solvent and ammonia gas is purged to precipitate the pure O,O-DMDTPA.$NH_3$ salt;

vi) the above obtain O,O-DMDTPA.$NH_3$ salt is subjected to neutralization with concentrated sulphuric acid to get O,O-DMDTPA;

vii) the O,O-DMDTPA obtained in the above step is once again purified through ammonia salt formation and neutralization method as mentioned in above steps v) and vi) to get chromatographically pure O,O-DMDTPA;

viii) adding the above obtain pure O,O-DMDTPA to diethyl maleate at low temperature of −30 to −25° C. in four lots, each at regular interval of 20 minutes;

ix) maintain the above reaction mass at temperature of −30 to −25° C. for the period of 4 hours;

x) water wash the above mass to remove O,O-DMDTPA;

xi) treating the above obtain crude Malathion with sulfur reagent at 5 to 10° C. for the period of 13 hours;

xii) crystallizing the above obtained Malathion from methanol at low temperature and xiii) drying the above obtain mass with anhydrous sodium sulphate in isopropanol to obtain Malathion of formula (I).

Accordingly, there is provided an improved process for the preparation of intermediate O,O-DMDTPA having formula (II), which is used in step (viii) of process of preparation of Malathion of formula (I),

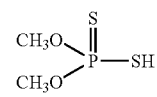
(II)

which comprises:

i) adding methanol to phosphorous sulfide in organic solvent at 25-50° C. for the period of 1.5-2 hours;

ii) stirring the above suspension for the period of 5-6 hours at 50-55° C.;

iii) expelling the $H_2S$ gas with nitrogen, after cooling the above suspension to 25-28° C.;

iv) filtering the above suspension to remove insoluble impurities to obtain crude O,O-DMDTPA;

v) the crude O,O-DMDTPA is subjected to dissolution in suitable solvent and ammonia gas is purged to precipitate the pure O,O-DMDTPA.$NH_3$ salt;

vi) the above obtain O,O-DMDTPA.NH₃ salt is subjected to neutralization with concentrated sulphuric acid to get O,O-DMDTPA and vii) the O,O-DMDTPA obtained in the above step is once again purified through ammonia salt formation and neutralization method as mentioned in above steps v) and vi) to get chromatographically pure O,O-DMDTPA.

In the step (i) of the above preparation, phosphorous sulfide used in the reaction can be selected from phosphorus pentasulfide, tetraphosphorus heptasulfide and tetraphosphorus decasulfide and preferably using phosphorus pentasulfide. Solvent used in the reaction can be selected from group consisting of hexane, benzene, toluene, diethyl ether, chloroform, ethyl acetate and dichloromethane and preferably using toluene.

In the step (iii) of the above preparation, expel the H₂S gas with nitrogen, after cooling the above suspension to 25-28° C. If H₂S is present, it will react with diethyl maleate to afford diethyl-2-mercaptosuccinate and dimerize to form tetraethyl dithiodisuccinate.

In the step (iv) of the above preparation, the insoluble impurities may be any unreacted solids. Example: Phosphorus sulfide.

In the step (v) of the above preparation, the solvent used in reaction can be selected from hexane, benzene, toluene, diethyl ether, chloroform, ethyl acetate and dichloromethane and preferably using ethyl acetate. In this step, ammonia gas is purged in the reaction vessel at temperature of −10 to 5° C. till $p^H$ of 9.5-9.8 is reached and preferably at a temperature in the range from −5 to 0° C. The duration of the reaction may range from 1 to 4 hours, preferably for the period of 2 hours.

In the step (vi) of the above preparation, the reaction temperature may range from −30 to −15° C. and preferably at a temperature of −20° C. The duration of the reaction may range from 10 to 30 minutes, preferably for the period of 20 minutes.

In the step (viii) of the above preparation, the molar ratio of diethyl maleate to O,O-DMDTPA in reaction is 1:2.5 and preferably using the molar ratio of diethyl maleate to O,O-DMDTPA is 1:2.0

In the step (x) of the above preparation, water washing is carried out to remove water soluble impurities, at 10 to 15° C. until the $p^H$ of last water wash is found to be 6.5 to 7.0.

In the step (xi) of the above preparation, the sulfide reagent used in reaction can be selected from sodium sulfide, potassium sulfide, phosphorus pentasulfide, calcium sulfide, ammonium sulfide and ammonium bisulfide and preferably using phosphorus pentasulfide. An aqueous solution of sulfide reagent used in this step of reaction is usually 3%.

In the step (xii) of the above preparation, crystallization of above obtain Malathion from methanol at temperature of −45 to −25° C. and preferably at a temperature in the range from −40 to −30° C.

In the step (xiii) of the above preparation, the reaction temperature may range from 15 to 40° C. and preferably at a temperature in the range from 25 to 27° C. The duration of the reaction may range from 5 to 9 hours, preferably for the period of 7 hours. The water content of isopropanol used in the reaction must below 0.05%.

The Malathion prepared by the process of this invention is storage stable. Specially, after storage at 8-15° C. for the period of 6 months, the Malathion has following purity/impurity profile i. greater than about 99.5% (w/w) Malathion.
ii. less than 0.09% of Isomalathion
iii. less than 0.03 of O,O,S-trimethyl phosphorodithioate
iv. less than 0.002% of diethyl fumarate
v. less than 0.1% of unknown impurities
vi. less than 0.21 of total impurities and
vii. water content is less than 0.02%.

The details of the invention are given in the examples provided below, which are given to illustrate the invention only and therefore should not be construed to limit the scope of the invention

EXAMPLE 1

Preparation of Crude O,O-Dimethyl Dithio Phosphoric Acid

Step (i): Preparation of Crude O,O-Dimethyl Dithio Phosphoric Acid

To 4-necked flask (1 L) equipped with mechanical stirrer, thermometer pocket, pressure equalizing funnel and nitrogen atmosphere, was charged toluene (150 mL, Kf<0.1%) and phosphoruspentasulfide (222 grams) at room temperature. An alkali scrubber was used to trap hydrogen sulfide gas released during the reaction. Methanol (150 grams, Kf<0.1%) was added to the above reaction mass at 25-35° C. for the period of 1.5-2 hours. After the addition of methanol, temperature of the above reaction mass was raised to 50° C. and maintained the temperature at 50-55° C. for a period of 5 hours. The evolution of hydrogen sulfide gas was confirmed by checking with lead acetate paper and the reaction mass was cooled to 25-28° C. and nitrogen gas was purged for 20-30 minutes to expel traces of hydrogen sulfide gas presented. The reaction mass was then filtered through hy-flow bed to remove any unreacted phosphorus pentasulfide and washed with toluene (150 mL). Layer separation was done to remove a small amount of lower layer, and upper toluene layer was taken for concentration under vacuum at 45-50° C. and concentrated till toluene content was found to be below 5%, which is monitored by HPLC.

Yield: 260-270 grams.
HPLC purity: 87.21%.

Step (ii): Preparation of 1ˢᵗ Ammonium Salt of O,O-DMDTPA

To 4-necked flask (5 L) equipped with mechanical stirrer, thermometer pocket and gas sparger, was charged ethyl acetate (2.7 L) and crude O,O-DMDTPA (270 grams) (obtained from Step (i)). Cooled the above reaction mass to −5° C. and purged the ammonia gas in the reaction vessel at a temperature of −5-0° C. till pH was reached to 9.5-9.8. After the desired pH was achieved, reaction mass was maintained at −5 to 0° C. for a period of 2 hours. The reaction mass was then filtered and washed with ethyl acetate (270 mL). Suck dried and unloaded. The wet weight of obtained ammonium salt was 240-255 grams. Dried at 25-28° C. under vacuum for the period of 5 hours or till constant weight was achieved.
The dry weight of ammonium salt was 233-240 grams.
HPLC purity: 99.33%.

Step (iii): Regeneration of Ammonium Salt of O,O-DMDTPA

To 4-necked flask (3 L) equipped with mechanical stirrer, thermometer pocket and pressure-equalizing funnel, was charged dichloromethane (1.68 L). Cooled the above reaction mass to −25 to −20° C. and concentrated sulphuric acid (65 grams) was charged in the pressure equalizing funnel and added to the above reaction mass drop wise at temperature of −25 to −20° C. Maintained the above reaction mass at −20° C. for 20 minutes and pH of dichloromethane layer was checked as per above pH checking process to obtain pH below 2.0. The temperature of the reaction mass was raised to 25° C. in 30-35 minutes and stirred for the period of 2 hours. The above reaction mass was filtered and washed with dichloromethane (233 mL). The filtered ammonium sulphate containing compound was once again stirred with dichloromethane (1.165 L) for a period of 2 hours and the ammonium sulphate was filtered and washed with dichloromethane (233 mL). The dichloromethane layers were combined and concentrated at 30-35° C. under vacuum till constant weight was achieved. The weight of regenerated O,O-DMDTPA was 184-188 grams and ammonium sulphate was 105-112 grams. If weight of ammonium sulphate is more than theoretical weight, stirred once with dichloromethane.

HPLC purity: 98.09%.

Step (iv): Preparation of $2^{nd}$ Ammonium Salt of O,O-DMDTPA

To 4-necked flask (3 L) equipped with mechanical stirrer, thermometer pocket and gas sparge, was charged ethyl acetate (1.84 L) and regenerated O,O-DMDTPA (184 grams) (obtained from step (iii)). Cooled the above reaction mass to −5° C. and purged the ammonia gas in the reaction vessel at a temperature of −5 to 0° C. till pH of 9.5-9.8 was reached. After the desired pH was achieved, reaction mass was maintained at −5 to 0° C. for the period of 2 hours. The above reaction mass was then filtered and washed with ethyl acetate (184 mL). Suck dried and unloaded. The wet weight of obtained ammonium salt was 172-175 grams. Dried at 25-28° C. under vacuum for the period of 5 hours or till constant weight was achieved. The dry weight of ammonium salt was 162-166 grams.

HPLC purity: 99.68%

Step (v): Regeneration of $2^{nd}$ Ammonium Salt of O,O-DMDTPA

To 4-necked flask (3 L) equipped with mechanical stirrer, thermometer pocket and pressure-equalizing funnel, was charged dichloromethane (1.204 L). Cooled the above reaction mass to −25 to −20° C. Concentrated sulphuric acid (46 grams) was charged in the pressure equalizing funnel and added to the above reaction mass drop wise at −25 to −20° C. and maintain the above reaction mass at −20° C. for a period of 20 minutes. $p^H$ of dichloromethane layer was checked as per above pH checking process to obtain the pH below 2.0. The temperature of the reaction mass was raised to 25° C. in 30-35 minutes and stirred for a period of 2 hours. The above reaction mass was filtered and washed with dichloromethane (163 mL). The filtered ammonium sulphate containing compound was once again stirred with dichloromethane (860 mL) for a period of 2 hours and ammonium sulphate was filtered and washed with dichloromethane (163 mL). The dichloromethane layers were combined and concentrated at 30-35° C. under vacuum till constant weight was achieved. The weight of regenerated O,O-DMDTPA was 123-126 grams and ammonium sulphate was 74-80 grams. If weight of ammonium sulphate is more than theoretical weight, stirred once with dichloromethane.

HPCL purity: 97.84%.

IR spectra (cm$^{-1}$): 1016.23;

$^1$H NMR (400 MHz, CD$_3$OD): δ 3.0343 (singlet, 1H), 3.83-3.87 (2 singlets, 6H).

EXAMPLE 2

Preparation of Malathion

Step (i): Preparation of Crude Malathion

To 4-necked flask (0.5 L) equipped with mechanical stirrer, thermometer pocket and nitrogen atmosphere, was charged O,O-DMDTPA (126 grams, 0.797 M) (obtained from Example 1). Cooled the above reaction mass to −30 to −25° C. and add diethyl maleate (55 grams, 0.319 M, GC purity: 97%) in 4 lots (each 13.8 grams) at regular interval of 20 minutes at −30 to −25° C., and maintained the above reaction mass temperature at −30 to −25° C. for the period of 4 hours. The sample was analyzed after 4 hours to check the diethyl maleate content below 1% by HPLC before proceeding for workup. If the diethyl maleate was found to be more than 1% the above reaction mass was maintained for another one hour at the same temperature and again analyzed by HPLC. After the diethyl maleate content was found to be less than 1% by HPLC, the above reaction mass temperature was raised to 5-10° C. and washed with demineralized water (181 mL) for 6 times. pH of last water wash was checked and found to be 6.5-7.5. In case the pH is not in range, one more water wash needs to be done. The sample was analyzed to check the O,O-DMDTPA content below 0.05% by HPLC.

Yield: 110-112 grams.

Step (ii): Removal of Diethyl Fumarate from Crude Malathion

Crude Malathion (111 grams) (obtained from step (i)) was stirred with 3% sodium sulphide solution (111 mL) at 10-15° C. for the period of 13 hours. HPLC analysis of the sample after 13 hours showed diethyl fumarate not more than 0.1%. Both layers were separated and organic layer was washed with demineralised water (111 mL) for 6 times by maintaining temperature at 10-15° C. till pH of 6.5-7.5. was achieved.

Yield: 80 grams.

Step (iii): Purification of Malathion

To a 4-necked flask (0.5 L) equipped with mechanical stirrer, thermometer pocket and calcium chloride guard tube, was charged methanol (160 mL) and Malathion (80 grams). The reaction mass was cooled to −40 to −35° C. slowly when formation of white solid was observed. Methanol (160 mL) was once again added and reaction mass temperature is raised to −10° C. The above reaction mass was cooled once again to −30 to −25° C. and maintained for period of 30 minutes. Methanol (240 mL) was siphoned out from the above reaction mass and temperature thereafter raised from 8 to 10° C. To the above reaction, add dichloromethane (160 mL) and demineralized water and stirred at 10° C. for the period of 10 minutes. The layers were separated, aqueous layer volume was measured and found to be 240 mL. To the dichloromethane layer, add demineralized water (160 mL) and stirred at temperature of 5-10° C. for the period of 10 minutes. The layers were separated, aqueous layer volume was measured and found to be 160 mL. The dichloromethane layer was dried over anhydrous dried sodium sulphate (8.0 gram), filtered washed with dichloromethane (40 mL). This dichloromethane layer was filtered through 0.5□ filter paper, concentrated at 25-30° C. under vacuum to obtain pure Malathion.

Yield: 57 grams.

Step (iv): Drying of Malathion

The pure Malathion (57 grams) (obtained from step (iii)) was filtered through 0.5□ filter paper under nitrogen atmosphere and charged to a 4-necked flask (0.5 L) equipped with mechanical stirrer, thermometer pocket and nitrogen atmosphere. Add isopropanol (275 mL, Kf<0.05%) and anhydrous dried sodium sulphate (27 grams) at 25-27° C. and stirred for the period of 7 hours at 25-27° C. The water content after 7 hours of stirring was checked and found to be 0.16%. The mass was filtered through filter paper no. 1 under nitrogen atmosphere and washed with isopropanol (30 mL). This mass was again filtered through 0.5□. filter paper under nitrogen and washed with isopropanol (25 mL). The filtrate was concentrated under 5-10 mm Hg vacuum and maintain temperature at 25-27° C. for a period of 9 hours. The dried Malathion was carefully unloaded under nitrogen atmosphere and water content was checked and found to be less than 0.1%.

IR spectra (cm$^{-1}$): 1737.28, 1016.23;
$^1$H NMR (400 MHz, CD$_3$OD): δ 1.22-1.32 (2 triplets, 6H), 2.90-3.76 (2 quartets, 4H), 3.80-3.81 (2 doublets, 6H), 4.11-4.21 (multiplet, 3H).

EXAMPLE 3

Analysis of Sample Batches of Malathion Prepared by this Process

In Table II set forth below, three different batches of Malathion are prepared by the process of present invention (noted as A, B, C) were analyzed by HPLC for the identification of purity and impurities. After storage at 8-15° C. for the period of 6 months:

TABLE II

| | Batch No. | | |
|---|---|---|---|
| Analysis | A | B | C |
| HPLC assay | 99.8% | 99.8% | 99.5% |
| Iso S-[1,2-(dicarbethoxy)-ethyl]O,O-dimethyl phosphorodithioate | 0.06% | 0.07% | 0.09% |
| Malaoxon | Nil | Nil | Nil |
| S-imp O,O,S-trimethyl phosphorodithioate | 0.03% | 0.03% | 0.01% |
| Diethyl maleate | Nil | Nil | Nil |
| Diethyl fumarate | 0.002% | 0.001% | 0.002% |
| O,O-DMDTPA | Nil | Nil | Nil |
| Unknown impurities | 0.12% | 0.20% | 0.11% |
| Total impurities | 0.21% | 0.3% | 0.21% |
| Water content | 0.04% | 0.02% | 0.04% |

We claim:
1. A process for the preparation of Malathion of formula (I),

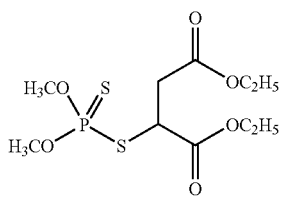

(I)

which comprises the steps of:
i) adding methanol to phosphorous sulfide in organic solvent at 25-50° C. for a period of 1.5-2 hours;
ii) stirring the above suspension for a period of 5-6 hours at 50-55° C.;
iii) expelling the H$_2$S gas with nitrogen, after cooling the above suspension to 25-28° C.;
iv) filtering the above suspension to remove insoluble impurities to obtain crude O,O-DMDTPA;
v) the crude O,O-DMDTPA is subjected to dissolution in suitable solvent and ammonia gas is purged to precipitate pure O,O-DMDTPA.NH$_3$ salt;
vi) the above obtain O,O-DMDTPA.NH$_3$ salt is subjected to neutralization with concentrated sulphuric acid to get O,O-DMDTPA;
vii) the O,O-DMDTPA obtained in the above step is once again purified through ammonia salt formation and neutralization method as mentioned in above steps v) and vi) to get chromatographically pure O,O-DMDTPA of the formula II

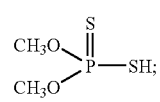

(II)

viii) adding the above obtain pure O,O-DMDTPA to diethyl maleate at low temperature of −30 to −25° C. in four lots, each at regular interval of 20 minutes;
ix) maintaining the above reaction mass at temperature of −30 to −25° C. for a period of 4 hours;
x) water washing the above mass to remove O,O-DMDTPA;
xi) treating the above obtain crude Malathion with a sulfur reagent at 5 to 10° C. for a period of 13 hours;
xii) crystallizing the above obtained Malathion from methanol at low temperature and
xiii) drying the above obtain mass with anhydrous sodium sulphate in isopropanol to obtain Malathion of formula (I).
2. A process for the preparation of intermediate O,O-dimethyldithiophosphoric acid of formula (II)

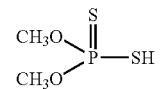

(II)

for use in the preparation of Malathion, which comprises the steps of:
i) adding methanol to phosphorous sulfide in organic solvent at 25-50° C. for a period of 1.5-2 hours;
ii) stirring the above suspension for a period of 5-6 hours at 50-55° C.;
iii) expelling the H$_2$S gas with nitrogen, after cooling the above suspension to 25-28° C.;
iv) filtering the above suspension to remove insoluble impurities to obtain crude O,O-DMDTPA;
v) the crude O,O-DMDTPA is subjected to dissolution in ethyl acetate and ammonia gas is purged to precipitate the pure O,O-DMDTPA.NH$_3$ salt;
vi) the above obtain O,O-DMDTPA.NH$_3$ salt is subjected to neutralization with concentrated sulphuric acid to get O,O-DMDTPA and vii) the O,O-DMDTPA obtained in the above step is once again purified through ammonia salt formation and neutralization method as mentioned in above steps v) and vi) to get chromatographically pure product.

3. The process as claimed in claim 1, wherein said phosphorous sulfide is selected from phosphorus pentasulfide, tetraphosphorus heptasulfide and tetraphosphorus decasulfide.

4. The process as claimed in claim 1, wherein said organic solvent is selected from hexane, benzene, toluene, diethyl ether, chloroform, ethyl acetate and dichloromethane.

5. The process as claimed in claim 1, wherein in step v) the duration of the reaction ranges from 1 to 4 hours.

6. The process as claimed in claim 1, wherein in step (viii), molar ratio of diethyl maleate to O,O-DMDTPA is 1:2.5.

7. The process as claimed in claim 1, wherein said sulfur reagent used in step xi) is selected from sodium sulfide, potassium sulfide, calcium sulfide, ammonium sulfide and ammonium bisulfide.

8. The process as claimed in claim 1, wherein in step xii) malathion is crystallized from methanol at temperature in the range of −45 to −25° C.

9. The process as claimed in claim 1, wherein in step xiii) the drying temperature ranges from 15 to 40° C.

10. The process as claimed in claim 1, wherein in step xiii) the duration of the drying ranges from 5 to 9 hours.

11. The process as claimed in claim 1, wherein in step xiii) the water content of isopropanol used is below 0.05%.

12. The process as claimed in claim 1, wherein said Malathion prepared by the process of claim 1, after storage at 8-15° C. for a period of 6 months, has the following purity/impurity profile:
  i. greater than about 99.5% (w/w) Malathion
  ii. less than 0.09% of Isomalathion
  iii. less than 0.03% of O,O,S-trimethyl phosphorodithioate
  iv. less than 0.002% of diethyl fumarate
  v. less than 0.1% of unknown impurities
  vi. less than 0.21% of total impurities and
  vii. water content is less than 0.02%.

13. The process as claimed in claim 2, wherein said phosphorous sulfide is selected from phosphorus pentasulfide, tetraphosphorus heptasulfide and tetraphosphorus decasulfide.

14. The process as claimed in claim 2, wherein said organic solvent is selected from hexane, benzene, toluene, diethyl ether, chloroform, ethyl acetate and dichloromethane.

15. The process as claimed in claim 2, wherein in step v) the duration of the reaction ranges from 1 to 4 hours.

* * * * *